US012697135B2

(12) United States Patent
Kaethner et al.

(10) Patent No.: US 12,697,135 B2
(45) Date of Patent: Aug. 4, 2026

(54) THREADING SUPPORT FACILITY FOR THREADING AN OBJECT INTO A GUIDE APPARATUS

(71) Applicant: Siemens Healthcare GmbH, Erlangen (DE)

(72) Inventors: Christian Kaethner, Forchheim (DE); Andreas Meyer, Bubenreuth (DE); Michael Wiets, Langensendelbach (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 1463 days.

(21) Appl. No.: 17/337,869

(22) Filed: Jun. 3, 2021

(65) Prior Publication Data

US 2021/0386453 A1 Dec. 16, 2021

(30) Foreign Application Priority Data

Jun. 15, 2020 (DE) ..................... 10 2020 207 365.1

(51) Int. Cl.
  *A61B 17/34* (2006.01)
  *A61B 17/00* (2006.01)
(52) U.S. Cl.
  CPC .............................. *A61B 17/3417* (2013.01); *A61B 2017/00026* (2013.01); *A61B 2017/00057* (2013.01);
  (Continued)
(58) Field of Classification Search
  None
  See application file for complete search history.

(56) References Cited

U.S. PATENT DOCUMENTS 6,299,576 B1 10/2001 Ouchi
10,765,836 B1 * 9/2020 Gottlieb ................ A61M 25/09
(Continued)

FOREIGN PATENT DOCUMENTS

CN 101103899 A 1/2008
CN 101991898 A 3/2011
(Continued)

OTHER PUBLICATIONS

Braun Hospicare Ltd. (2011). Askina® Gel Amorphous Hydrogel. (Year: 2011).*
(Continued)

*Primary Examiner* — Charles A Marmor, II
*Assistant Examiner* — Marc D. Honrath
(74) *Attorney, Agent, or Firm* — Harness, Dickey & Pierce, P.L.C.

(57) ABSTRACT

A threading support facility is for threading an object into a guide apparatus. The threading support facility is connectable to the guide apparatus and is configured to support threading of the object into the guide apparatus. In an embodiment, the threading support facility includes a wall connecting a first aperture of the threading support facility and a second aperture of the threading support facility. The first aperture is embodied as an inlet for insertion of the object into the threading support facility and the second aperture is embodied as an outlet out of the threading support facility. Further, a sub-guide runs along the wall of the threading support facility and runs in a direction from the first aperture to the second aperture. The sub-guide is configured to support guiding of the object, after insertion through the first aperture, into the threading support facility in a direction of the second aperture.

19 Claims, 4 Drawing Sheets

(52) U.S. Cl.
CPC .............. *A61B 2017/00876* (2013.01); *A61B 2017/3407* (2013.01); *A61B 2017/3458* (2013.01); *A61B 2017/348* (2013.01)

(56) References Cited

U.S. PATENT DOCUMENTS

| | | | |
|---|---|---|---|
| 2004/0073193 A1 | 4/2004 | Houser et al. | |
| 2004/0260237 A1 | 12/2004 | Squadrito | |
| 2005/0173659 A1 | 8/2005 | Jespersen et al. | |
| 2006/0094987 A1 | 5/2006 | van Erp et al. | |
| 2006/0116691 A1 | 6/2006 | Bonacci | |
| 2009/0171152 A1 | 7/2009 | Aoki et al. | |
| 2010/0217275 A1 * | 8/2010 | Carmeli | A61M 25/09 |
| | | | 606/128 |
| 2012/0078072 A1 | 3/2012 | Roesicke et al. | |
| 2012/0296313 A1 | 11/2012 | Andreacchi et al. | |
| 2013/0053827 A1 | 2/2013 | Schippel et al. | |
| 2013/0211382 A1 | 8/2013 | Mouri et al. | |
| 2014/0094836 A1 | 4/2014 | Feng et al. | |
| 2015/0025315 A1 * | 1/2015 | Nishina | A61B 10/0275 |
| | | | 600/104 |
| 2015/0258270 A1 | 9/2015 | Kunis | |
| 2016/0287346 A1 | 10/2016 | Hyodo et al. | |
| 2017/0035458 A1 | 2/2017 | Hashiguchi | |
| 2017/0035996 A1 | 2/2017 | O'Fallon | |
| 2017/0172390 A1 | 6/2017 | Fu et al. | |
| 2017/0325928 A1 | 11/2017 | Ino et al. | |
| 2018/0055337 A1 | 3/2018 | Kabushiki | |
| 2019/0351183 A1 | 11/2019 | Ishida | |

FOREIGN PATENT DOCUMENTS

| | | | | |
|---|---|---|---|---|
| CN | 102438508 A | 5/2012 | | |
| CN | 102793577 A | 11/2012 | | |
| CN | 103239790 A | 8/2013 | | |
| CN | 103717253 A | 4/2014 | | |
| CN | 103945818 A | 7/2014 | | |
| CN | 106232022 A | 12/2016 | | |
| CN | 106422031 A | 2/2017 | | |
| CN | 106714713 A | 5/2017 | | |
| CN | 109475399 A | 3/2019 | | |
| CN | 109890449 A | 6/2019 | | |
| CN | 110811927 A | 2/2020 | | |
| DE | 102010048908 A1 * | 4/2012 | ........ | A61B 17/0057 |
| EP | 2821001 A1 | 1/2015 | | |
| JP | 2016016210 A | 2/2016 | | |
| JP | 2016050821 A * | 4/2016 | | |
| WO | WO-2006119422 A2 * | 11/2006 | ........ | A61M 25/0043 |
| WO | WO-2019213215 A1 * | 11/2019 | ............ | A61B 34/20 |

OTHER PUBLICATIONS

German Office Action for German Application No. 102020207365.1 dated Mar. 26, 2021.

* cited by examiner

THREADING SUPPORT FACILITY FOR THREADING AN OBJECT INTO A GUIDE APPARATUS

PRIORITY STATEMENT

The present application hereby claims priority under 35 U.S.C. § 119 to German patent application number DE 102020207365.1 filed Jun. 15, 2020, the entire contents of which are hereby incorporated herein by reference.

FIELD

Example embodiments of the invention generally relate to a threading support facility for threading an object into a guide apparatus. Example embodiments of the invention further relate to a guide apparatus.

BACKGROUND

In the course of an interventional medical procedure it is often necessary to thread an object or a medical object into a guide apparatus. Here the medical object is typically elongated and flexible. The medical object can be a catheter and/or a guide wire and/or an endoscope, for example. The guide apparatus can be in particular part of a robotic system for guiding the medical object during the interventional procedure and/or it can be a port.

Threading the medical object into the guide apparatus is typically done manually. Yet threading is often time-consuming and requires a great deal of fine motor skills.

SUMMARY

The inventors have discovered that the medical object often has to be threaded into a small aperture, the area of which is barely greater than a cross-sectional area of the medical object. In addition, the inventors have discovered that the medical object can bend or snap off during threading or otherwise be obstructed, which makes the threading process more difficult.

At least one embodiment of the present invention therefore provides a facility that allows simple threading of an object into a guide apparatus.

At least one embodiment of the present invention provides a threading support facility for threading an object into a guide apparatus and by a guide apparatus. Advantageous developments are set out in the claims and in the description that follows.

At least one embodiment of the present invention relates to a threading support facility for threading an object into a guide apparatus. Here the threading support facility is embodied to be connected to the guide apparatus. Moreover, the threading support facility is embodied to support threading of the object into the guide apparatus. The threading support facility has a first aperture and a second aperture, wherein the first and the second aperture are connected to each other by a wall. The first aperture is embodied as an inlet for inserting the object into the threading support facility and the second aperture is embodied as an outlet out of the threading support facility. The threading support facility comprises a sub-guide apparatus, the sub-guide apparatus being arranged along the wall of the threading support facility. The sub-guide apparatus runs in a direction from the first aperture to the second aperture. The sub-guide apparatus is embodied to support guiding of the object that has been inserted through the first aperture into the threading support facility in the direction of the second aperture.

At least one embodiment of the invention also relates to a guide apparatus that includes at least one embodiment of the aforementioned threading support facility, with the guide apparatus being embodied to guide an object.

The guide apparatus is embodied, in at least one embodiment, in particular to guide the object. The guide apparatus can be embodied in particular as described in the aforementioned embodiments. The threading support facility is embodied as described in the aforementioned and serves the purpose of simplifying and accelerating the threading of the object into the guide apparatus.

At least one embodiment of the invention also relates to a threading support facility for threading an object into a guide apparatus, the threading support facility being connectable to the guide apparatus and being configured to support threading of the object into the guide apparatus, the threading support facility comprising:

a wall connecting a first aperture of the threading support facility and a second aperture of the threading support facility, the first aperture being embodied as an inlet for insertion of the object into the threading support facility and the second aperture being embodied as an outlet out of the threading support facility a wall connecting a first aperture of the threading support facility and a second aperture of the threading support facility, the first aperture being embodied as an inlet for insertion of the object into the threading support facility and the second aperture being embodied as an outlet out of the threading support facility, and a sub-guide apparatus running along the wall of the threading support facility and running in a direction from the first aperture to the second aperture, the sub-guide apparatus being configured to support guiding of the object, after insertion through the first aperture, into the threading support facility in a direction of the second aperture.

At least one embodiment of the invention also relates to a threading support facility for threading an object into a guide apparatus, the threading support facility being connectable to the guide apparatus and being configured to support threading of the object into the guide apparatus, the threading support facility comprising:

a first aperture and a second aperture connected by a wall of the threading support facility, the first aperture being configured as an inlet for insertion of the object into the threading support facility and the second aperture being configured as an outlet out of the threading support facility; and a sub-guide apparatus, the sub-guide apparatus running along the wall of the threading support facility and running in a direction from the first aperture to the second aperture, the sub-guide apparatus being configured to support guiding of the object, after insertion through the first aperture, into the threading support facility in a direction of the second aperture.

BRIEF DESCRIPTION OF THE DRAWINGS

The aforementioned properties, features and advantages of the present invention will emerge more clearly and comprehensibly in conjunction with the figures that follow and from the descriptions thereof. However, the figures and the descriptions thereof are not intended to restrict the invention and embodiments thereof in any way. In the various figures, components that remain the same are denoted by the same reference signs. The figures are generally not true to scale.

The drawing shows.

DETAILED DESCRIPTION OF THE EXAMPLE EMBODIMENTS

Figure 1:
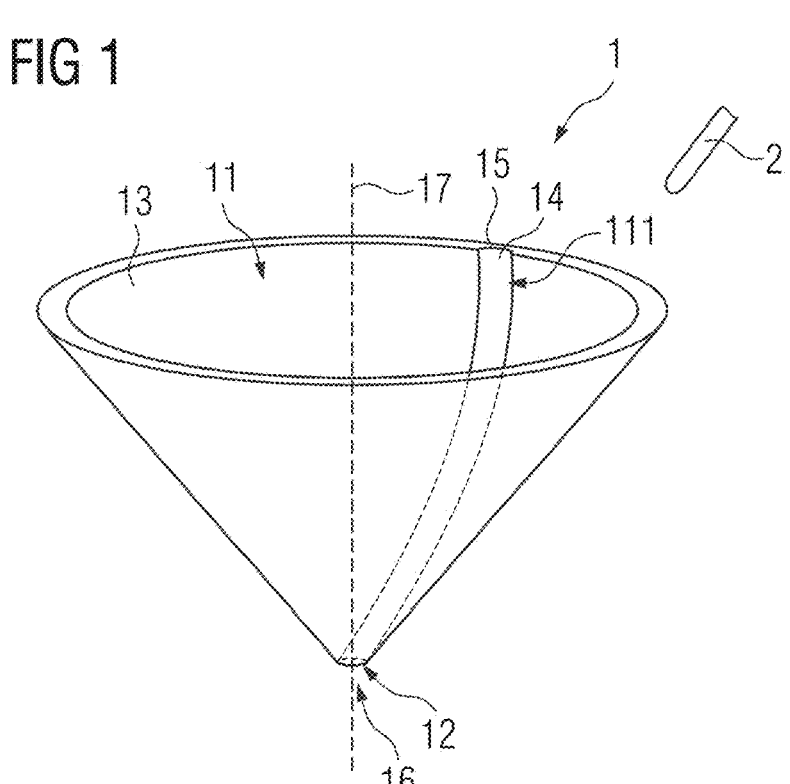
FIG. 1 a first example embodiment of a threading support facility according to the invention, FIG. 2 a second example embodiment of a threading support facility according to the invention, FIG. 3 a third example embodiment of a threading support facility according to the invention, FIG. 4 a fourth example embodiment of a threading support facility according to the invention that includes a sensor, FIG. 5 a fifth example embodiment of a threading support facility according to the invention that includes a multiplicity of sensors, FIG. 6 a sixth example embodiment of a threading support facility according to the invention, FIG. 7 a seventh example embodiment of a threading support facility according to the invention that includes a multiplicity of magnetically active sub-regions, FIG. 8 an example embodiment of a guide apparatus that includes a threading support facility according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the present invention relates to a threading support facility for threading an object into a guide apparatus. Here the threading support facility is embodied to be connected to the guide apparatus. Moreover, the threading support facility is embodied to support threading of the object into the guide apparatus. The threading support facility has a first aperture and a second aperture, wherein the first and the second aperture are connected to each other by a wall. The first aperture is embodied as an inlet for inserting the object into the threading support facility and the second aperture is embodied as an outlet out of the threading support facility. The threading support facility comprises a sub-guide apparatus, the sub-guide apparatus being arranged along the wall of the threading support facility. The sub-guide apparatus runs in a direction from the first aperture to the second aperture. The sub-guide apparatus is embodied to support guiding of the object that has been inserted through the first aperture into the threading support facility in the direction of the second aperture.

In particular, the object can be a medical object. In particular, the medical object can be a surgical instrument and/or diagnostic instrument, for example. In particular, the medical object can be elongated and/or flexible. The medical object can be embodied as a catheter and/or endoscope and/or guide wire, for example. In particular, the medical object can be an infusion tube. In particular, the object can be an optical fiber.

In particular, the guide apparatus can be a part of a robotic system for guiding the object. In particular, the robotic system can be embodied to guide the object during a medical, interventional procedure or during an interventional, medical intervention. Alternatively, the guide apparatus can be a port system or a port. Here the port system can be an implantable (subcutaneous) catheter system, which can be tapped from outside, for example.

In particular, the threading support facility is embodied to simplify the threading of the object into the guide apparatus.

In particular, the threading support facility can become or be connected to the guide apparatus. In particular, this connection can be detachable or fixed. In particular, the connection can be achieved using a clip system or a screw system or a plug system or a hook system. In other words, the connection can be embodied as a clip connection or screw connection or plug connection or hook connection. In particular, the connection can be soldered or riveted. In particular, at least one part of the guide apparatus and one part of the threading support facility can be embodied in a single piece. Embodied in a single piece means that the parts are combined in one component. In particular, the component can be manufactured from a single piece. In the case of the connections described, it is possible to refer to a direct connection. Alternatively, the threading support facility can be indirectly connected to the guide apparatus. In other words, the threading support facility can be connected to the guide apparatus via an intermediate fixture. Here the object can be guided initially out of the second aperture in the threading support facility into the intermediate fixture. From the intermediate fixture the object is then guided into the guide apparatus. Here the intermediate fixture can be a continuation of an object guide for the object in the guide apparatus. In other words, the intermediate fixture can be connected to the threading support facility and to the guide apparatus such that the object is further guided from the second aperture in the threading support facility through the intermediate fixture into the guide apparatus. The connection between the intermediate fixture and the threading support facility and the connection between the intermediate fixture and the guide apparatus can also be embodied as a clip connection or screw connection or plug connection or hook connection or rivet connection or soldered connection or be embodied in one piece. For example, the intermediate fixture can be a disinfecting apparatus for disinfecting the object. In other words, the threading support facility can be connected to the guide apparatus via a disinfecting apparatus.

In particular, the threading support facility has the first and the second aperture. In other words, the threading support facility includes the first and the second aperture. In particular, the first aperture serves as the inlet for threading the object into the threading support facility. In particular, the second aperture serves as the outlet for the object out of the threading support facility. In particular, on the outlet or on the second aperture, the threading support facility is directly or indirectly connected to the guide apparatus. In particular, the object is threaded into the guide apparatus via the second aperture. In particular, the object can be threaded by a medical professional through the first aperture into the threading support facility. The medical professional can be a physician, a nurse and/or another medical professional. In particular, the first and/or second aperture can have a circular or oval or angular or square or rectangular or polygonal shape. In other words, an area of the first and/or the second aperture can include such a shape. In particular, the shape of the first aperture can correspond to the shape of the second aperture. Alternatively, the shapes of the two apertures can differ.

The first and the second aperture are connected by the wall. In particular, the wall describes the area of the connection within the two apertures. In other words, the wall describes an inner wall in the connection between the first and the second aperture. The wall or area includes in particular the first and the second aperture along its respective perimeter. In particular, the wall can describe the shortest connection between the two apertures. In particular, the shape or embodiment of the wall is dependent on the shape of the apertures. In particular, an area that is enclosed by a cross-section through the wall can include the same shape as the shape of the apertures if the shapes of the first and the second aperture are the same. In particular, a shortest distance between the first and the second aperture can amount to ca. 1 cm for example.

Moreover, the threading support facility comprises a sub-guide apparatus. In particular, the sub-guide apparatus is arranged on the wall. In particular, the sub-guide apparatus is embodied to guide the object in a direction from the first aperture to the second aperture. For this purpose, the sub-guide apparatus runs in a direction from the first aperture to the second aperture. In particular, the sub-guide apparatus can begin at the first aperture and end at the second aperture. Alternatively, the sub-guide apparatus can begin at any point on the wall of the threading support facility and end at the second aperture. Alternatively, the sub-guide apparatus can begin at any point on the wall or at the first aperture and end at any point on the wall closer to the second aperture. In other words "run in a direction from the first aperture to the second aperture" means in this context that the sub-guide apparatus ends at the second aperture or closer to the second than to the first aperture and, seen from the second aperture, begins on the wall in the direction of the first aperture. The sub-guide apparatus therefore includes a beginning and an end. The beginning describes the point or the place on the wall at which the sub-guide apparatus begins, and the end is arranged on the second aperture or in the vicinity of the second aperture. In particular, the sub-guide apparatus can run in a straight and/or curved line from the first aperture to the second aperture. A straight course of the sub-guide apparatus is described by the shortest distance between the beginning of the sub-guide apparatus and the end of the sub-guide apparatus. A curved course can be in particular a spiral-shaped or screw-shaped course. In particular, the sub-guide apparatus is embodied to support the guiding of the object in the direction of the outlet or second aperture. In particular, the object can be threaded into the first aperture in the threading support facility by the medical professional. In particular, the first aperture can be embodied to be large enough for the threading of the object to be achieved easily. In particular, the object can be threaded in the threading support facility by feeding the object independently into the sub-guide apparatus on the wall in the direction of the second aperture. In particular, the object can then be guided by feeding in the object without bending it or causing an obstruction in the sub-guide apparatus in the direction of the second aperture or of the outlet. In particular, feeding the object can be done manually by the medical professional. Alternatively, feeding the object can be achieved automatically. In particular, the sub-guide apparatus can be embodied such that the object barely has any play in the sub-guide apparatus.

The inventors have realized that the threading support facility allows complex threading into the guide apparatus to be avoided or simplified. In particular, the inventors have realized that the first aperture in the threading support facility can be embodied to be large enough for the object to be inserted or threaded easily into the first aperture. The insertion or threading of the object into the first aperture can be done manually. The inventors have realized that having a large enough first aperture saves time in the threading process and that fewer fine motor skills are necessary for the threading process. The inventors have realized in addition that the sub-guide apparatus makes it possible to prevent the object from being snapped inside the threading support facility and, due to having snapped, possibly not being able to be fed in as far as the second aperture.

According to one embodiment of the invention, the sub-guide apparatus is embodied as at least one groove in the wall of the threading support facility.

In particular, the groove can be embodied as a notch or a furrow. In particular, the groove can be adjusted to a shape of the object. In particular, the shape of the object can be described by a cross-sectional area of the object. For example, the cross-sectional area of the object can have a circular shape. In particular, the groove can then have a semi-circular cross-sectional area. In particular, a diameter of the semi-circular cross-sectional area can then be only slightly greater than a diameter of the cross-sectional area of the object. In particular, the diameter of the semi-circular cross-sectional area can be 5% or 10% or 20% greater than the diameter of the cross-sectional area of the object. In particular, the cross-sectional area of the groove can be rectangular or square or polygonal. In particular, the diameter of the cross-sectional area of the groove can then describe a width of the groove parallel to the wall. In particular, the width of the groove can be variable over its course along the wall.

In particular, the groove can be milled into the wall. Alternatively, the groove can be created in a process of casting the threading support facility. Alternatively, the groove can be created in a process of pressing the threading support facility. Alternatively, the groove can be created in a process of 3D printing the threading support facility.

In particular, the sub-guide apparatus can have more than one groove. In other words, the sub-guide apparatus can be embodied as more than one groove. In particular, each groove can run from the first aperture of the threading support facility to the second aperture of the threading support facility. In particular, the grooves can be arranged in parallel. In other words, the grooves do not then cross over in the wall. In particular, if a groove runs along a curved route in the wall, all the grooves can then have the same curvature. Alternatively, the radii of curvature of the curved grooves are different and the grooves are separated such that the grooves do not cross over each other in the wall.

The inventors have realized that the object in the at least one groove can be guided to the second aperture in the threading support facility if the diameter of the cross-sectional area of the groove is only slightly greater than the diameter of the cross-sectional area of the object. The inventors have realized that, in a threading support facility that can be used for different objects, the diameter of the sub-guide apparatus should be adjusted to the object with the greatest diameter of the cross-sectional area. The inventors have realized in addition that, if the sub-guide apparatus includes more than one groove, there is a greater probability that the object will thread autonomously into one of the grooves.

According to a further embodiment of the invention, the first aperture of the threading support facility has a larger area than the second aperture.

In other words, the threading support facility has a larger and a smaller aperture. In other words, the threading support facility includes a larger and a smaller aperture. The larger aperture corresponds to the first aperture, that is, to the inlet to the threading support facility and the smaller aperture corresponds to the second aperture, that is, to the outlet from the threading support facility. In particular, the shape of the apertures can be the same. Alternatively, the shape of the apertures can differ. In particular, the shape of at least one aperture can correspond to the shape of a cross-sectional area of the object. In particular, the area of the larger aperture can include a multiple of the cross-sectional area of the object. In particular, the area of the larger aperture can correspond to double or ten times or 20 times or 50 times or 100 times the cross-sectional area of the object. In particular, the area can correspond to a multiple that falls between the aforementioned values for the cross-sectional area. In particular, the small aperture can only be slightly smaller than the cross-sectional area. In particular, the small aperture can include an area that is five percent or ten percent or 20 percent or 50 percent greater than the cross-sectional area of the object. In particular, the area of the smaller aperture can be greater than the cross-sectional area by a factor that falls between the aforementioned factors. In particular, the area and shape of the smaller aperture can correspond to a cross-sectional area and shape of an object guide in the guide apparatus. In the object guide, the object is guided in the guide apparatus. In particular, the sub-guide apparatus can end in the smaller aperture. In other words, the second aperture can be directly connected to the object guide in the guide facility. In particular, the connection can be edge-free if the area and shape of the second aperture corresponds to the cross-sectional area and shape of the object guide at the connection.

The inventors have realized that having a large aperture as the inlet into the threading support facility makes threading easier. They have realized that time can be saved when threading the object and fewer fine motor skills are required than when the object is threaded directly into the guide apparatus. The inventors have realized in addition that smooth threading of the object into the guide apparatus can be guaranteed by the threading support facility if the area of the smaller aperture, that is, of the outlet of the threading support facility corresponds to the cross-sectional area of the object guide in the guide apparatus. Therefore, at the connection between the guide apparatus and the threading support facility, it is possible to avoid edges or corners on which the object can get caught and/or snap off.

According to a further embodiment of the invention, the first and the second aperture are connected to each other by the wall of the threading support facility in a funnel shape.

In other words, the wall of the threading support facility is shaped like a funnel. In particular, the first and the second aperture in the wall are connected to each other by a minimal area.

The inventors have realized that, due to the funnel shape, it is possible to avoid the object's snapping and/or getting caught when threading it through the threading support facility. In particular, it is possible to avoid the object bending back on itself in a U-shape before it passes through the second aperture and coming out of the threading support facility again through the first aperture. In addition, the inventors have realized that, due to the funnel shape, autonomous threading of the object into the sub-guide apparatus is facilitated.

According to a further embodiment of the invention, the sub-guide apparatus at least partly runs along the wall in a spiral shape around a connecting line between the first aperture and the second aperture.

The connecting line can run in particular through a respective center of the first and the second aperture. In particular, each of the two apertures has a center. These centers are connected by the connecting line. Here, the connecting line is the shortest connection between the centers. The center of an aperture can be located or arranged in particular in a center of gravity of the aperture. The center of gravity is also referred to as the "geometrical center of gravity" or "area center of gravity". In particular, in the case of a circular or square or rectangular aperture, the center can be the central point in the aperture.

In particular, spiral-shaped means that the sub-guide apparatus runs along the wall at least partly in the shape of a screw. In particular, spiral-shaped is used as a synonym for in the shape of a screw. As described in the aforementioned, the beginning of the sub-guide apparatus is arranged closer to the first aperture than is the end of the sub-guide apparatus. In other words, the end is arranged closer to the second aperture than is the beginning. The sub-guide apparatus runs from the beginning to the end on the wall of the threading support facility. In particular, the sub-guide apparatus then runs between the beginning and the end at least partly in the shape of a spiral or in the shape of a screw. Here the beginning and the end are arranged at a different angle relative to the connecting line. In particular, a difference in the angle between the beginning and the end can be defined. The difference in angle can be defined as the angle in the peripheral direction between the shortest connections from the beginning of the sub-guide apparatus to the connecting line and from the end of the sub-guide apparatus to the connecting line. The difference in angle can be between 0° and 360°. In particular, the difference in angle can be 5° or 10° or 20° or 30° or 40° or 50° or 60° or 70° or 80° or 90° or 100° or 150° or 200° or 250° or 300° or 350°. In particular, the difference in angle can fall between the values listed for possible differences in angle. In particular, the sub-guide apparatus can include at least one winding around the connecting line. This means that the sub-guide apparatus runs round the connecting line in the shape of a spiral or in the shape of a screw at least once by a full 360°. In other words, a winding means that the sub-guide apparatus runs along the wall 360° round the connecting line in the shape of a spiral or in the shape of a screw. In particular, the sub-guide apparatus can include more than one winding. Alternatively, the sub-guide apparatus does not have to include any winding. Then the beginning and the end are connected to each other by the sub-guide apparatus at least partly in the shape of a spiral or in the shape of a screw, without an additional winding.

In particular, at least one sub-section of the sub-guide apparatus does not have to run in the shape of a spiral or in the shape of a screw. In other words, a sub-section of the sub-guide apparatus can run in a straight line. A sub-section describes a section of the sub-guide apparatus. Here, in a straight line means that, in this section or sub-section, the sub-guide apparatus runs without any curvature. Alternatively, in a straight line can mean that the sub-section of the sub-guide apparatus runs along the wall in a projection parallel or perpendicular to the connecting line. In particular, the sub-section of the sub-guide apparatus that runs in a straight line can be arranged at the beginning and at the end of the sub-guide apparatus. Alternatively, or additionally, one or a plurality of straight sub-sections can be arranged between the beginning and the end of the sub-guide apparatus.

In particular, the sub-guide apparatus can include a multiplicity of grooves. In particular, the individual grooves are then at least partly arranged or interlaced in the shape of a spiral or of a screw such that they do not cross over each other. In particular, the grooves can be arranged in parallel.

The inventors have realized that a spiral shape or screw shape of the sub-guide apparatus simplifies the threading of the object. In particular, this increases the probability that the object will thread into the sub-guide apparatus autonomously. In addition, feeding the object into the threading support facility can be achieved in a particularly stable manner if the sub-guide apparatus runs at least partly in the shape of a spiral. Stable means that, throughout the entire threading process, the object is guided into the sub-guide apparatus and cannot slip out of it.

According to a further embodiment of the invention, the sub-guide apparatus has a first sub-aperture with a first area and a second sub-aperture with a second, smaller area. The first sub-aperture and the second sub-aperture are connected to each other by a sub-wall with a tapered cross-sectional area. Here the first sub-aperture is arranged on the first aperture of the threading support facility and the second sub-aperture on the second aperture of the threading support facility.

In particular, the second sub-aperture can correspond to the second aperture. In particular, the first sub-aperture can be arranged directly on the first aperture. Alternatively, the first sub-aperture can be arranged on the wall apart from the first aperture. In particular, "arranged on the first aperture" can mean that the first sub-aperture is arranged closer to the first aperture than the second sub-aperture is. In particular, the first sub-aperture corresponds to the beginning of the sub-guide apparatus and the second sub-aperture to the end of the sub-guide apparatus.

In particular, the first sub-aperture is embodied to be larger than the second sub-aperture. In other words, the first area of the first sub-aperture is larger than the second area of the second sub-aperture. In particular, the first sub-aperture corresponds to a large sub-aperture and the second sub-aperture to a small sub-aperture. In particular, the apertures are connected to each other by a sub-wall that has a tapered cross-sectional area. In particular, "tapered cross-sectional area" means that the cross-sectional area of the sub-guide apparatus becomes smaller in the direction of the second sub-aperture. In particular, the largest cross-sectional area in the sub-guide apparatus corresponds to the first sub-aperture and the smallest area in the sub-guide apparatus to the second sub-aperture. In particular, the cross-sectional area between the first sub-aperture and the second sub-aperture continually becomes smaller. In particular, the groove includes the sub-wall. In particular, the groove can be embodied in a funnel shape between the first and the second sub-aperture. In other words, the sub-wall of the groove can have a funnel shape that is open at one end.

In particular, the area of the first sub-aperture or the first area can be greater by a greater multiple than the cross-sectional area of the object. In particular, the area of the first sub-aperture or the first area can be greater by a greater multiple than the area of the second sub-aperture or the second area. In particular, the area of the second sub-aperture can be only slightly larger than the cross-sectional area of the object. For example, the area of the second sub-aperture can be only five percent or ten percent or 20 percent larger than the cross-sectional area of the object. The area of the first sub-aperture can be any amount larger than the cross-sectional area of the object. In particular, the area of the first sub-aperture can be twice as large or four times as large or ten times as large as the cross-sectional area of the object.

The inventors have realized that the tapered cross-sectional area of the sub-wall of the sub-guide apparatus facilitates direct threading of the object into the sub-guide apparatus for the medical professional. In particular, threading into the larger, first sub-aperture is less time-consuming and requires fewer fine motor skills than when the object is threaded directly into the object guide of the guide apparatus. This is helpful in particular when the first sub-aperture is arranged directly on the first aperture. In addition the inventors have realized that the tapered cross-sectional area facilitates autonomous threading of the object into the sub-guide apparatus. In particular the object threads particularly easily in the regions in which the cross-sectional area of the sub-guide apparatus is clearly larger than a cross-sectional area of the object. However, due to the cross-sectional area of the sub-guide apparatus being tapered toward the second aperture, the object can be guided precisely since the object always has less clearance in the sub-guide apparatus in the direction of the second sub-aperture.

According to a further embodiment of the invention, the threading support facility includes at least one sensor, which is embodied to detect successful threading of the object through the threading support facility.

In particular, the sensor can detect when the object passes through the second aperture of the threading support facility. In other words, the sensor detects when the object has been successfully pushed through the second aperture.

In embodiments, the sensor can also detect the feeding in of the object. In other words, the sensor can detect how far the object has already been fed through the threading support facility. In particular, the sensor can detect a tip of the object. The tip of the object is the region of the object that is fed first through the second aperture or passes through the second aperture first. The tip can include for example, between 0.5 cm and 2 cm of the object.

The sensor can include an imaging sensor. Alternatively or additionally, the sensor can include an electrical sensor. Alternatively or additionally, the sensor can include an optical sensor.

The inventors have realized that a working procedure for medical professionals can be optimized if the medical professional receives feedback on the successful threading, via the sensor. In this way, the medical professional can detect when the object has become caught in the threading support facility and/or is obstructed in another way and/or has snapped and therefore cannot pass through the second aperture of the threading support facility. In addition, the inventors have realized that in this way it is possible to prevent the object being damaged due to being fed in too fiercely if it becomes caught up, is obstructed and/or has snapped.

According to a further embodiment of the invention, the sensor includes at least one light sensor.

In particular, the light-sensor can be embodied as a photoelectric barrier. In particular, the photoelectric barrier can include a transmitter and a receiver. In particular, the transmitter can be embodied to emit light, in particular optical light. The receiver can be embodied to receive or detect this optical light. In particular, the transmitter and the receiver can be embodied such that the light transmitted by the transmitter falls onto the receiver such that the receiver can detect the light. In particular, the at least one light sensor can be arranged on the second aperture or on the second sub-aperture. In particular, the transmitter can be arranged on one side of the second aperture and the receiver can be arranged on the opposite side of the second aperture. In particular, the at least one light sensor that is embodied as a light barrier can be arranged such that the light barrier is penetrated when the object is fed through the second aperture or passes through the second aperture. In particular, penetration of the light barrier then indicates successful threading of the object through the threading support facility. Penetration of the light barrier means that the object shields the light transmitted by the transmitter such that the receiver detects less or no light.

In embodiments, a multiplicity of light sensors can be arranged in the threading support facility. In particular, the multiplicity of light sensors can be arranged along the sub-guide apparatus. In particular, the light sensors that constitute the multiplicity of light sensors can be embodied as a multiplicity of light barriers. In particular, the light sensors that constitute the multiplicity of light sensors can be arranged such that one light sensor detects in each case that the object has passed through a sub-section of the sub-guide apparatus. In particular, the object then penetrates the light barrier. In other words, the multiplicity of light sensors can be arranged such that the sub-guide apparatus is divided into a multiplicity of sub-sections. A light sensor is arranged in each case at the end of the sub-section. If the light sensor detects the object, the medical professional can then assume that the sub-section of the sub-guide apparatus arranged in front of the corresponding light sensor has been passed through successfully. In particular, the sub-sections of the sub-guide apparatus can be equal in size. Alternatively, the sub-sections can be of different sizes.

Alternatively, the multiplicity of light sensors in the threading support facility can be arranged such that passage of the object through a sub-section of the threading support facility is detected even when the object is not threaded in the sub-guide apparatus. For this purpose, the multiplicity of light sensors can be arranged on the wall of the threading support facility, for example. In particular, the multiplicity of light sensors can be arranged randomly on the wall. Alternatively, the multiplicity of light sensors can be arranged on the wall at fixed intervals apart from one another.

The inventors have realized that a light sensor is a simple device for detecting the passage of the object and therefore of providing information on successful threading. In addition, the inventors have realized that applying a multiplicity of light sensors has the advantage that the medical professional knows into which sub-section of the threading support facility the object has already been fed. This is particularly helpful when troubleshooting if the object has become caught up and/or is obstructed and/or has snapped.

According to a further embodiment of the invention, the sensor includes at least one impedance sensor.

In particular, the impedance sensor serves the purpose of detecting the passage of the object past the impedance sensor. In particular, the impedance sensor can be arranged on the second aperture of the threading support facility or on the second sub-aperture. In order for it to be able to be detected by the impedance sensor, at least one sub-region of the object must be electrically conductive and/or magnetically active. In particular, the tip of the object can be electrically conductive and/or magnetically active. In particular, the impedance sensor can then detect when the tip or the electrically conductive and/or magnetically active sub-region of the object passes through the impedance sensor or is pushed past it.

In particular, the impedance sensor can be embodied to be inductive. For this purpose, the tip or at least one sub-region of the object is embodied to be magnetically active. For this purpose, the impedance sensor is embodied as a coil. The coil can be arranged on the sub-guide apparatus such that, for example, the object is pushed through the coil when the object is threaded in the sub-guide apparatus. In particular, the coil can be arranged around the second aperture such that the object is pushed through the coil when it passes through the second aperture to leave the threading support facility. In particular, the passage of the object through the coil can produce an induction voltage in the coil. In particular, this induction voltage can be measured. In particular, this induction voltage can act as a sensor signal that indicates or displays the passage of or successful threading of the object.

In embodiments, more than one impedance sensor or a multiplicity of impedance sensors can be arranged in the threading support facility. This multiplicity of impedance sensors can be arranged in a similar way to that described for the arrangement of the multiplicity of light sensors in the threading support facility.

The inventors have realized that an impedance sensor offers a further option for detecting the feeding or the successful threading of the object through the threading support facility. The inventors have realized that the impedance sensor is suitable in particular for detecting objects with at least one electrically conductive and/or magnetically active sub-region and/or tip. The inventors have realized that in this way successful threading of the object through the threading support facility can be reported back to the medical professional.

According to a further embodiment of the invention, the threading support facility includes an X-ray sensor.

In particular, the X-ray sensor can include an X-ray source and an X-ray detector. In particular, the X-ray source can be embodied to emit X-rays. In particular, the X-ray detector can be embodied to detect X-rays. In particular, the X-ray source can be a transmission anode X-ray source or a rotating anode X-ray source. In particular, the X-ray detector can be a flat image detector or an X-ray flat image detector. The detector can be a semiconductor or a scintillation X-ray detector. In particular, the X-ray detector can be a digital X-ray detector.

In particular, the X-ray source is embodied such that the X-rays emitted are detected by the X-ray detector. In particular, the threading support facility is arranged between the X-ray source and the X-ray detector. In particular, the X-ray detector can detect or acquire or record an X-ray image at least of the second aperture of the threading support facility when the aperture is irradiated with X-rays. In particular, the X-ray detector can detect or acquire or record an X-ray image of the threading support facility when the facility is irradiated with X-rays. In particular, a material-specific absorption coefficient of a material from which the threading support facility is manufactured differs from a material-specific absorption coefficient of a material of the object. In particular, at least one sub-region of the object can be manufactured from this material. In particular, the absorption coefficient of the material of the threading support facility can be lower than the absorption coefficient of the material of the object. For example, the threading support facility can be manufactured from a plastic and the object from a metal. In particular, at least one sub-region of the object can be manufactured from a material that is visible in the X-ray image. In particular, the material of the object can also be an alloy. In particular, the material of the object can be stainless steel, for example, and/or polytetrafluorethylene (PTFE or Teflon). In particular, the object can include in a sub-region what is known as a "radiopaque length" that is visible in the X-ray image.

In particular, the X-ray detector can detect X-ray images continuously. Alternatively, the X-ray detector can be primed by the medical professional to detect an individual X-ray image. In particular, at least the position of the sub-region of the object that is visible in the X-ray image can then be determined. In particular, it is then possible to determine whether the object has passed through the second aperture and whether the threading was successful.

The inventors have realized that with an X-ray sensor it is particularly easy to determine or detect at any time the position or the feeding of the object in the threading support facility. In addition, the inventors have realized that it is possible with the X-ray sensor to detect any possible position of the object in the threading support facility. In addition, the inventors have realized that many objects that are embodied for a medical application include what is known as a "radiopaque length". In medical applications this is provided so that it is possible to see the object in an X-ray image of a patient. The inventors have realized that the "radiopaque length" can also be used to detect the position or the feeding of or the successful threading of the object through the threading support facility.

According to a further embodiment of the invention, the sensor includes a camera.

In particular, the camera can be arranged on the second aperture or on the second sub-aperture of the threading support facility. In particular, the camera can be embodied to acquire optical images. In particular, the camera can determine when the object passes through the second aperture. In particular, the camera can therefore detect successful threading.

The inventors have realized that, with a conventional camera, the successful threading of the object through the threading support facility can be detected. In addition, the inventors have realized that the camera can provide the medical professional with a visual impression.

According to a further embodiment of the invention, the threading support facility includes a lubricant dispenser to dispense a lubricant to increase the sliding capacity of the object on the wall and/or sub-wall.

In particular, when the lubricant dispenser dispenses the lubricant, it automatically moistens the wall and/or the sub-wall with the lubricant. In particular, the lubricant dispenser can moisten the wall and/or the sub-wall with the lubricant at set intervals. Alternatively or additionally, the lubricant dispenser can moisten the wall and/or the sub-wall with the lubricant before the object is threaded through the threading support facility.

In particular, "moisten" means that the lubricant is applied as a thin layer on the wall and/or the sub-wall. It is for this reason that the lubricant dispenser dispenses the lubricant.

In particular, the lubricant can be dripped through the first aperture of the threading support facility into the threading support facility or applied on the wall and/or the sub-wall. In particular, such a small amount of lubricant is dripped into the threading support facility that no or very little lubricant comes out of the second aperture.

Alternatively, the lubricant can be atomized by the lubricant dispenser and sprayed in this way onto the wall and/or sub-wall.

Alternatively, the lubricant dispenser can be activated by the medical professional. In particular, after activation of a button or a lever or a pump lever, the lubricant dispenser can moisten the wall and/or the sub-wall with the lubricant or dispense the lubricant. Alternatively, the medical professional can apply the lubricant manually, with a finger for example, from the lubricant dispenser onto the wall and/or the sub-wall. The lubricant dispenser can then be a vessel, for example. The vessel can be a glass or plastic bottle, for example.

In particular, when lubricant is used, the threading support facility can be manufactured from, for example, silicone or a plastic or ceramic, as used in a 3D printing process, or from medical-grade stainless steel or from any plastic or any ceramic. In particular, the wall and/or the sub-wall of the threading support facility can be manufactured from at least one of these materials. In particular, at least the wall and/or the sub-wall can be coated with one of these materials. In particular, the threading support facility can therefore be manufactured by 3D printing or by a casting process or a pressing process and so on.

In particular, water or a sodium chloride (NaCl) solution, for example, can be used as a lubricant.

The inventors have realized that moistening the wall and/or the sub-wall with a lubricant simplifies the threading of the object. In particular, feeding in the object can be simplified by the lubricant since the object slides more easily down the wall and/or sub-wall that has been moistened with lubricant. A probability of the object getting caught or stuck on a wall and/or sub-wall that has been moistened with lubricant can therefore be minimized.

According to a possible embodiment of the invention, the wall and/or the sub-wall is manufactured from polytetrafluorethylene.

In particular, the entire threading support facility can be manufactured from polytetrafluorethylene (PTFE). Alternatively, the wall and/or the sub-wall can be coated with PTFE.

The inventors have realized that the object slides particularly well on PTFE. Therefore, no lubricant is necessary to simplify the threading of the object through the threading support facility if the wall and/or the sub-wall is made from PTFE or is coated with PTFE.

According to a further embodiment of the invention, the object and the threading support facility each include at least one magnetically active sub-region. Here the at least one magnetically active sub-region of the threading support facility is arranged on the second aperture of the threading support facility.

In particular, the at least one magnetically active sub-region of the threading support facility can include a ferromagnetic material. In particular, the at least one magnetically active sub-region of the threading support facility can be a permanent magnet. Alternatively, the at least one magnetically active sub-region of the threading support facility can be an electromagnet. In particular, a magnetic effect of the electromagnet can be activated and deactivated or turned on and off. In other words, the at least one magnetically active sub-region of the threading support facility can be activated and deactivated or turned on and off, when it is embodied as an electromagnet. In particular, the electromagnet can be activated or turned on when the object is in the vicinity of the electromagnet.

In particular, the magnetically active sub-region of the object can include the tip of the object. In other words, the tip of the object in particular can be embodied to be magnetically active. In particular, the magnetically active sub-region of the object can be embodied from a ferromagnetic material. In particular, the tip of the object can include a permanent magnet. Alternatively, the tip of the object can include an electromagnet. In particular, the tip of the object can then be pulled in the direction of the magnetically active sub-region of the threading support facility by a magnetic effect of the magnetically active sub-region of the threading support facility. In particular, the magnetically active sub-region of the threading support facility can be arranged such that the object is pulled in the direction of the second aperture. In particular, the magnetically active sub-region of the threading support facility is arranged in turn on the second aperture of the threading support facility. Alternatively, a different sub-region from the tip of the object can be embodied to be magnetically active. In particular, the magnetically active sub-region of the object can encompass the entire object.

The inventors have realized that the threading of the object through the threading support facility via a magnetically active sub-region of the threading support facility, which acts at least at times magnetically on a magnetically active sub-region of the object, can be simplified. In particular, the tip of the object can be prevented from folding back on itself when the tip is drawn through the magnetically active sub-region of the threading support facility. In particular, the magnetically active sub-region of the threading support facility can act supportively on the second aperture to guide the object out of the threading support facility through the second aperture.

According to a further embodiment of the invention, a multiplicity of magnetically active sub-regions of the threading support facility are arranged along the sub-guide apparatus. Here the multiplicity of magnetically active sub-regions of the threading support facility can be activated independently of one another. The multiplicity of magnetically active sub-regions of the threading support facility can be activated such that they guide the magnetically active sub-region of the object in the threading support facility.

In particular, the multiplicity of magnetically active sub-regions of the threading support facility is embodied as a multiplicity of electromagnets. In particular, the electromagnets can attract the magnetically active sub-region of the object. In particular, the electromagnets can be activated one after the other. In other words, the electromagnets can be activated in a row or in a sequence. In particular, an electromagnet can be activated during the process of threading through the threading support facility. In particular, the first electromagnet to be activated is the one that is arranged at the shortest distance from the first aperture. The next electromagnet to be activated is the one that is arranged at the shortest distance from the last active electromagnet. In the process, the last electromagnet to be active is deactivated. This sequence is continued. The last electromagnet in this sequence is arranged on the second aperture or on the second sub-aperture of the threading support facility. In particular, the electromagnets can be arranged along the sub-guide apparatus from the first aperture to the second aperture. In this way, the object can be guided along the sub-guide apparatus. In particular, no manual feeding of the object into the threading support facility is necessary. If the sub-guide apparatus includes more than one groove, such a series of electromagnets can be arranged on each of the grooves. In particular, all the electromagnets that are the same distance from one of the apertures can be activated simultaneously. In particular, only one electromagnet per groove is activated simultaneously.

The inventors have realized that, with a series of activatable electromagnets, it is possible to guide the object through the threading support facility and therefore accelerate the threading and make it less error-prone. In addition, the inventors have realized that with the aid of the electromagnets, the independent threading of the object into the sub-guide apparatus can be supported and accelerated.

At least one embodiment of the invention also relates to a guide apparatus that includes at least one embodiment of the aforementioned threading support facility, with the guide apparatus being embodied to guide an object.

The guide apparatus is embodied, in at least one embodiment, in particular to guide the object. The guide apparatus can be embodied in particular as described in the aforementioned embodiments. The threading support facility is embodied as described in the aforementioned and serves the purpose of simplifying and accelerating the threading of the object into the guide apparatus.

The inventors have realized that the threading support facility can be connected or combined with the guide apparatus in order to simplify and accelerate the threading of the object into the guide apparatus.

FIG. 1 shows a first example embodiment of a threading support facility according to the invention 1.

The threading support facility 1 includes a first aperture 11 and a second aperture 12. One area of the first aperture 11 is a multiplicity of times larger, for example 20 times larger, than an area of the second aperture 12. In the example embodiment shown here, the area of the second aperture 12 is only slightly larger than a cross-sectional area of an object 2 that is to be threaded through the threading support facility 1 into a guide apparatus 5. The second aperture 12 can be ten percent larger, for example, than the cross-sectional area of the object 2. In particular, the object 2 can be a medical object. In particular, the object 2 can be a guide wire or a catheter or an optical fiber, etc. The threading support facility 1 additionally includes a wall 13.

The first aperture 11 and the second aperture 12 are connected in a funnel shape via the wall 13. The wall 13 describes the internal connection between the two apertures 11, 12. The first and the second aperture can be spaced ca. 1 cm apart, for example. The threading support facility 1 additionally includes a sub-guide apparatus 111. The sub-guide apparatus 111 is arranged along the wall 13. The sub-guide apparatus 111 includes a first sub-aperture 15 and a second sub-aperture 16. The first sub-aperture 15 includes a larger area than the second sub-aperture 16. The second sub-aperture 16 corresponds to the second aperture 12. Therefore, an area of the second sub-aperture 16 is only slightly larger than the cross-sectional area of the object 2. In particular, the area of the second sub-aperture 16 can be ten percent larger, for example, than the cross-sectional area of the object 2. In addition, the area of the second sub-aperture 16 and the cross-sectional area of the object 2 can have the same shape. In particular, both areas can be circular. An area of the first sub-aperture 15 can be twice as large, for example, as half the cross-sectional area of the object 2. In particular, the area of the first sub-aperture 15 and the half cross-sectional area of the object 2 can have the same shape, in particular a semi-circular shape. The first sub-aperture 15 is arranged on the first aperture 11 of the threading support facility 1. The first sub-aperture 15 and the second sub-aperture 16 are connected by a sub-wall with a tapered cross-sectional area. In particular, the first sub-aperture 15 and the second sub-aperture 16 can be connected in a funnel shape with a half-open funnel. In alternative example embodiments, the first sub-aperture 15 and the second sub-aperture 16 can be equal in size. The connection or the sub-wall runs in the shape of a groove 14 in the wall 13. The groove 14 runs in the shape of a spiral or in the shape of a screw along the wall 13 in a direction from the first sub-aperture 15 to the second sub-aperture 16. The spiral- or screw shape runs round a connecting line 17 between a center or central point or center of gravity in the first aperture 11 and a center or central point or center of gravity in the second aperture 12. In alternative example embodiments, only at least one part of the groove 14 runs in the shape of a spiral or in the shape of a screw. In particular, a sub-section of the groove 14 can run in a straight line. In particular, a sub-section of the groove 14 by the first sub-aperture 15 and/or a sub-section of the groove 14 by the second sub-aperture 16 or a sub-section of the groove 14 between the apertures 15, 16 can run in a straight line. In alternative embodiments, the entire groove 14 can run in a straight line. In particular, the groove 14 then runs along a shortest distance on the wall 13 in a direction from the first aperture 11 to the second aperture 12.

Figure 2:
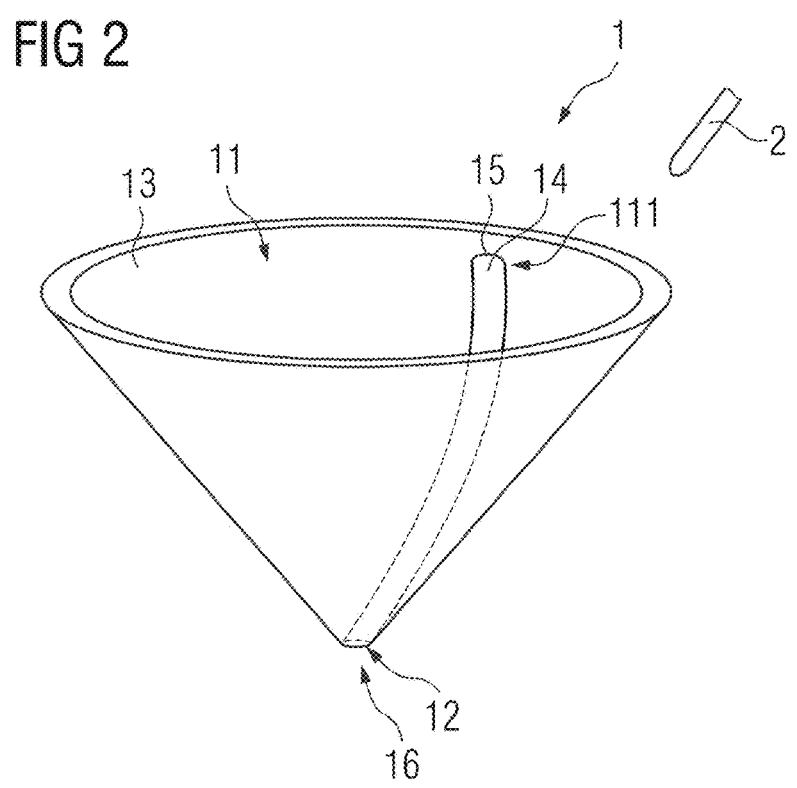

FIG. 2 shows a second example embodiment of a threading support facility according to the invention 1.

The example embodiment of the threading support facility 1 shown in FIG. 2 mostly corresponds to the example embodiment shown in FIG. 1.

However, the first sub-aperture 15 of the sub-guide apparatus 111 is not directly arranged on the first aperture 11. The first sub-aperture 15 is arranged apart from the first aperture 11. In other words, the first sub-aperture 15 does not end at an edge of the threading support facility 1 on the first aperture 11.

Figure 3:
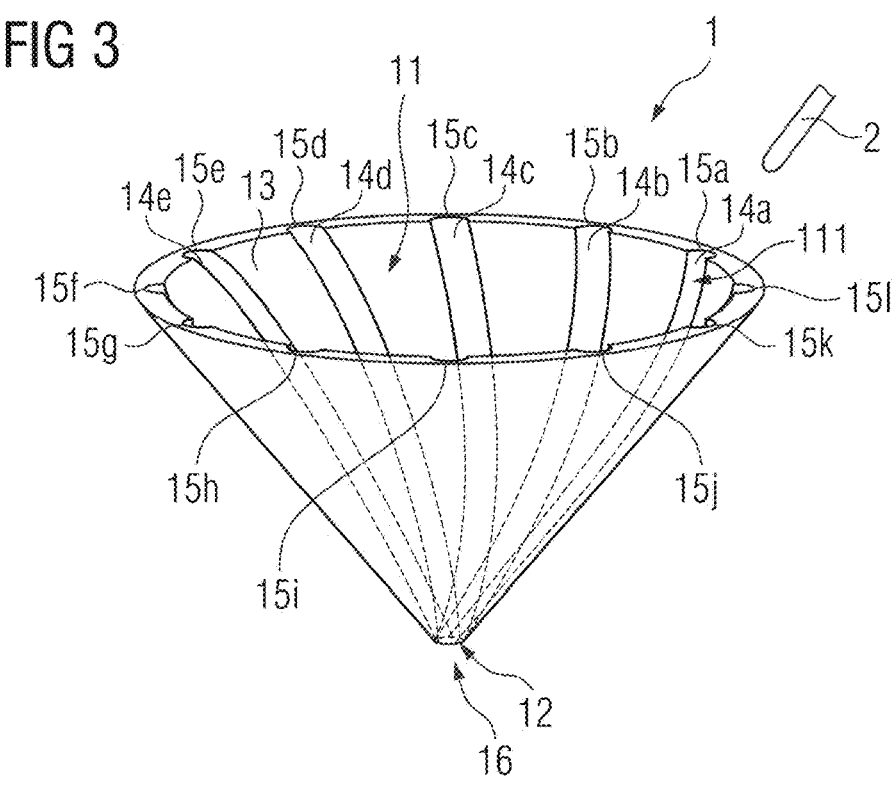

FIG. 3 shows a third example embodiment of a threading support facility according to the invention 1.

The example embodiment of the threading support facility 1 shown in FIG. 3 mostly corresponds to the example embodiment shown in FIG. 1.

In this example embodiment, the sub-guide apparatus 111 includes a multiplicity of grooves 14a, 14b, 14c, 14d, 14e. Here the grooves 14a, . . . , 14e can be arranged at random distances apart from one another. However, the grooves 14a, . . . , 14e should be arranged such that they are separable from one another and do not intersect or cross over each other. Each of these grooves 14a, . . . , 14e begins with a first sub-aperture 15a, 15b, 15c, 15d, 15e, 15f, 15g, 15h, 15i, 15j, 15k, 15l. Here some of the grooves that begin at the sub-apertures 15f, 15g, 15h, 15i, 15j, 15k, 151 and which are arranged on the side of the threading support facility 1 that is turned toward an observer of the figure cannot be seen in the view of the threading support facility 1 in FIG. 3. Each of these grooves 14a, . . . , 14e ends in a second sub-aperture 16, which is identical to the second aperture 12 of the threading support facility 1. All the grooves 14a, . . . , 14e run in parallel in a spiral- or screw shape along the wall 13. None of the grooves 14a, . . . , 14e crosses over with any other groove 14a, . . . , 14e.

In an alternative embodiment, the first sub-apertures 15a, . . . , 151 do not begin directly on the first aperture 11 but can be arranged at a distance apart from the large aperture 11 according to the second example embodiment from FIG. 2.

Figure 4:
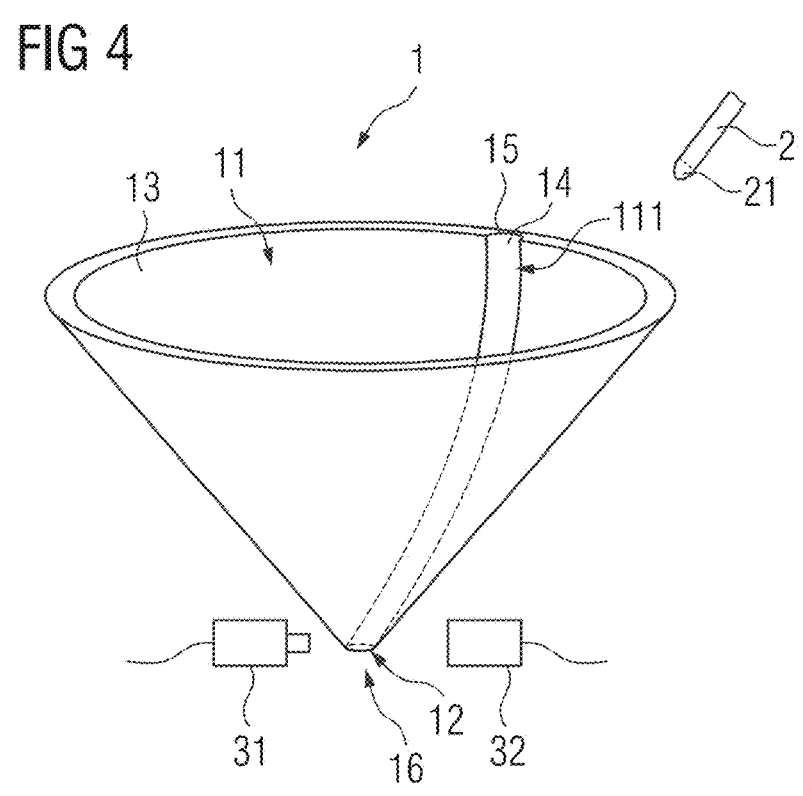

FIG. 4 shows a fourth example embodiment of a threading support facility according to the invention 1 including a sensor 31, 32.

The example embodiment of the threading support facility 1 shown in FIG. 4 mostly corresponds to the example embodiment shown in FIG. 1. The sub-guide apparatus 111 can be configured in alternative embodiments as described according to FIGS. 2 and 3.

In this example embodiment, a sensor is arranged on the second aperture 12 of the threading support facility 1. The sensor includes a transmitter 31 and a receiver 32. The sensor is embodied to detect successful threading of the object 2 through the threading support facility 1. In particular, the sensor can be a light sensor or a light barrier. In this case the transmitter 31 transmits light, which is detected by the receiver 32. If the object 2 is pushed through the second aperture 12, the object 2 blocks the transmitter 31 from the view of the receiver 32 and the receiver 32 does not receive any more light or receives less light. This signals the successful threading of the object 2 through the second aperture 12.

In alternative embodiments, the transmitter 31 can also be an X-ray source and the receiver 32 can be an X-ray detector. With the X-ray source and the X-ray detector, the second aperture 12 of the threading support facility 1 can be imaged and successful threading can be detected or deduced therefrom. In particular, the X-ray source and the X-ray detector can be embodied such that the entire threading support facility 1 can be imaged on the X-ray detector. Moreover, a position of the object 2 in the entire threading support facility 1 can therefore be detected.

In a further alternative embodiment, the sensor can include an impedance sensor. In particular, a sub-region of the object 2 can be embodied to be electrically conductive or magnetically active. The sub-region can be in particular a tip 21 of the object. If the tip 21 passes the impedance sensor, the impedance sensor measures a change in the impedance. From this, the successful threading can be detected or deduced.

In a further alternative embodiment, the sensor includes a camera. The camera can acquire at least one optical image of the second aperture 12. In particular, the camera can acquire a multiplicity of images. In this way, successful threading can be detected.

Figure 5:
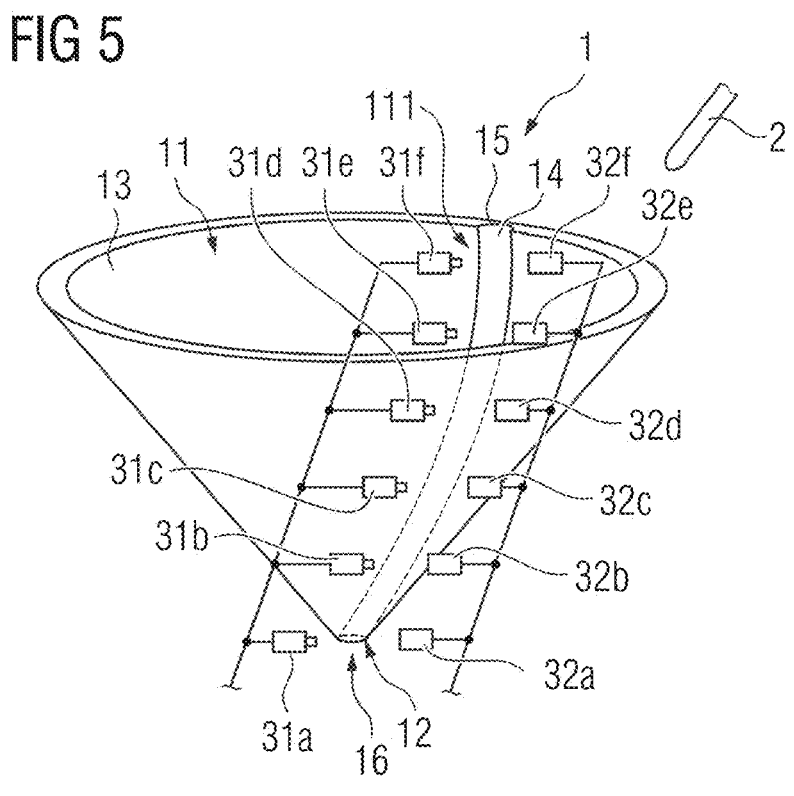

FIG. 5 shows a fifth example embodiment of a threading support facility according to the invention 1 including a multiplicity of sensors 31*a*, 31*b*, 31*c*, 31*d*, 31*e*, 31*f*, 32*a*, 32*b*, 32*c*, 32*d*, 32*e*, 32*f*.

The example embodiment of the threading support facility 1 shown in FIG. 4 mostly corresponds to the example embodiment shown in FIG. 1. The sub-guide apparatus 111 can be configured in alternative embodiments, as described in FIGS. 2 and 3.

Each of the sensors includes a transmitter 31*a*, 31*b*, 31*c*, 31*d*, 31*e*, 31*f* and a receiver 32*a*, 32*b*, 32*c*, 32*d*, 32*e*, 32*f*. A receiver 32*a*, . . . , 32*f* is assigned to each transmitter 31*a*, . . . , 31*f*. The sensors 31*a*, . . . , 32*f* are arranged along the sub-guide apparatus 111. The sensors 31*a*, . . . , 32*f* are arranged such that a transmitter 31*a*, . . . , 31*f*/receiver 32*a*, . . . , 32*f* pair "monitors" a sub-section of the sub-guide apparatus 111. If a transmitter 31*a*, . . . , 31*f*/receiver 32*a*, . . . , 32*f* pair detects a passage of the object 2, it can be assumed that the object 2 has successfully passed the sub-section of the sub-guide apparatus 111 located in front of the corresponding transmitter 31*a*, . . . , 31*f*/receiver 32*a*, . . . , 32*f* pair. In this case, "in front of" means the sub-section of the sub-guide apparatus 111 that is arranged closer to the first aperture 11 than the corresponding transmitter 31*a*, . . . , 31*f*/receiver 32*a*, . . . , 32*f* pair, which detects a passage of the object 2. Therefore, determination of the position of the object 2 inside the threading support facility 1 is possible.

The sensors can be embodied as disclosed in FIG. 4 of the description. In particular, the sensors can be embodied as a multiplicity of light sensors or light barriers.

Figure 6:
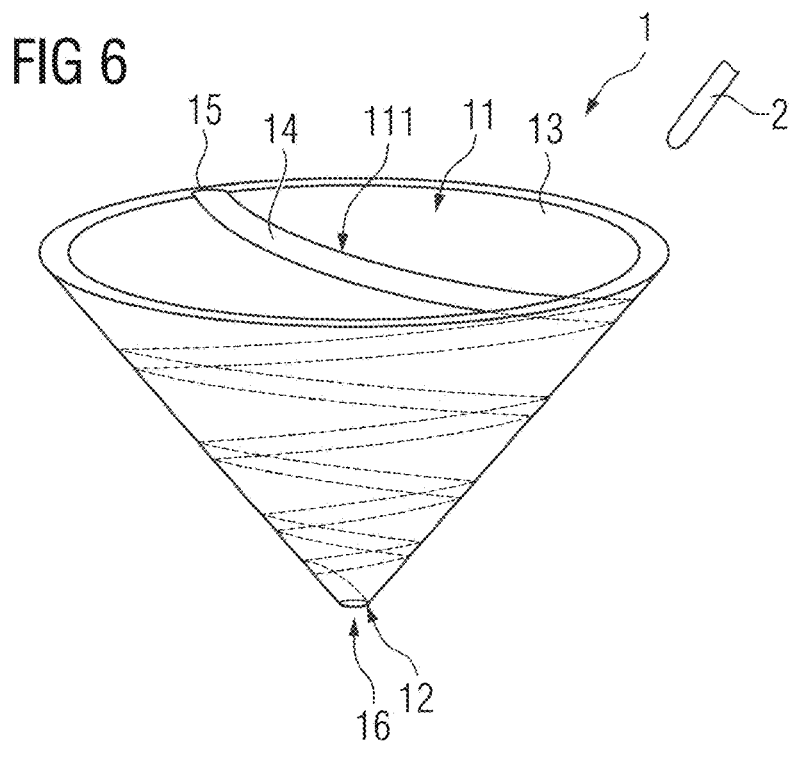

FIG. 6 shows a sixth example embodiment of a threading support facility according to the invention 1.

The threading support facility 1 includes a sub-guide apparatus 111, which includes a multiplicity of windings. In other words, in this example embodiment, the sub-guide apparatus 111 is arranged along the wall 13 such that it goes round a connecting line 17 between a center or central point or center of gravity in the first aperture 11 and a center or central point or center of gravity in the second aperture 12 a plurality of times. A winding corresponds to an "encircling" of the connecting line 17 by 360°. The sub-guide apparatus 111 is therefore embodied in the shape of a spiral or in the shape of a screw with a plurality of windings. There can be any number of windings.

All the example embodiments according to FIGS. 1 to 5 can alternatively include a sub-guide apparatus 111 that is embodied in such a manner.

Figure 7:
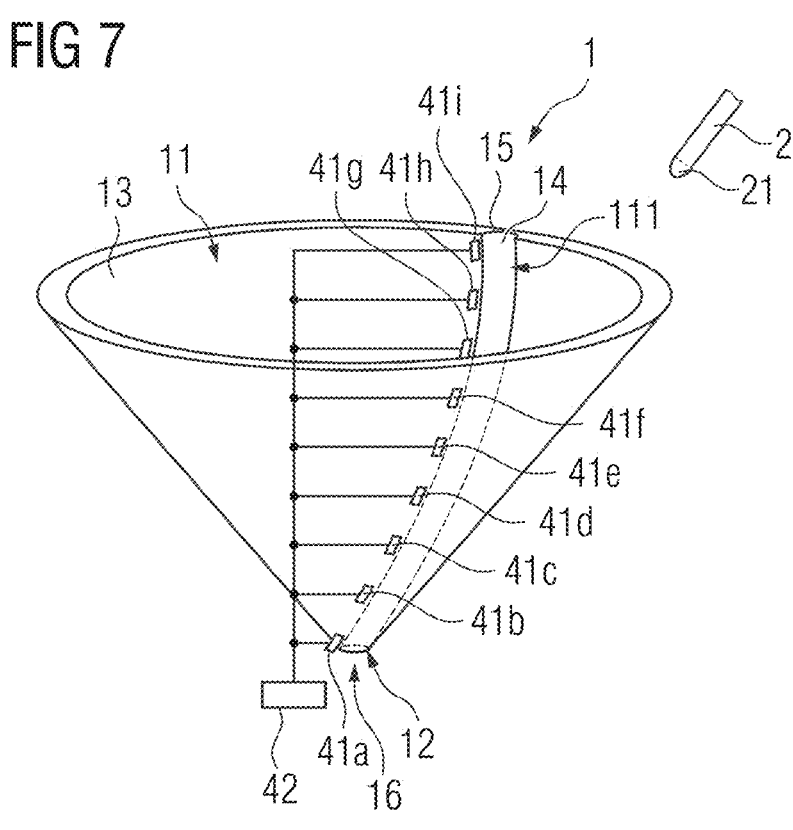

FIG. 7 shows a seventh example embodiment of a threading support facility according to the invention 1 including a multiplicity of magnetically active sub-regions 41*a*, 41*b*, 41*c*, 41*d*, 41*e*, 41*f*, 41*g*, 41*h*, 41*i*.

The example embodiment of the threading support facility 1 shown in FIG. 7 mostly corresponds to the example embodiment shown in FIG. 1. The threading support facility with a multiplicity of magnetically active sub-regions 41*a*, . . . , 41*i* can be configured in alternative embodiments as described in FIGS. 2 to 6.

Each magnetically active sub-region 41*a*, . . . , 41*i* is embodied as an electromagnet. In other words, the multiplicity of magnetically active sub-regions 41*a*, . . . , 41*i* corresponds to a plurality of electromagnets 41*a*, . . . , 41*i*. Therefore, each magnetically active sub-region 41*a*, . . . , 41*i* can be switched on or off or activated or deactivated. The plurality of electromagnets 41*a*, . . . , 41*i* are activated or deactivated via a control 42. The plurality of electromagnets 41*a*, . . . , 41*i* is arranged along the sub-guide apparatus 111. An electromagnet 41*i* is arranged on the second aperture 12 or on the second sub-aperture 16. The control 42 activates or deactivates the individual electromagnets 41*a*, . . . , 41*i* such that there is always only one electromagnet 41*a*, . . . , 41*i* that is activated. The electromagnets 41*a*, . . . , 41*i* are therefore activated in sequence, with the electromagnet 41*a*, which is the shortest distance away from the first aperture 11, being activated first. Then the electromagnet 41*b*, which is the shortest distance away from the last active electromagnet 41*a*, is activated. Finally, the electromagnet 41*i*, which is arranged on the second aperture 12, is activated. A sub-region of the object 2 is embodied to be magnetically active. In other words, the object has a magnetically active sub-region. The magnetically active sub-region can be embodied in particular as a ferromagnet or a permanent magnet or an electromagnet and so on. The magnetically active sub-region of the object can in particular be a tip 21 of the object 2. The tip 21 of the object 2 is the sub-region of the object 2 that is pushed first through the threading support facility 1. In other words, the tip 21 of the object 2 is the front sub-region of the object 2. The tip 21 can encompass 0.5 to 2 cm, for example. Alternatively, at least one other sub-region of the object 2 can be embodied to be magnetically active. By activating the electromagnets 41*a*, . . . , 41*i*, the object 2 can gradually be "pulled" or guided by the sub-guide apparatus 111. An active, manual feeding of the object 2 is therefore not necessary in order to move the object 2 in the direction of the second aperture 12. The object 2 can be guided from the first aperture 11 to the second aperture 12 with the aid of the electromagnets 41*a*, . . . , 41*i*. The number of electromagnets 41*a*, . . . , 41*i* is any desired.

In an alternative example embodiment, only one magnetically active sub-region 41*i* of the threading support facility 1 can be arranged on the second aperture 12 or on the second sub-aperture 16. The magnetically active sub-region 41*i* of the threading support facility 1 can in this case be embodied as a ferromagnet or a permanent magnet or an electromagnet. The tip 21 of the object 2 is likewise embodied to be magnetically active. The magnetically active sub-region 41*i* of the threading support facility 1 helps to guide the tip 21 of the object 2 when the object 2 is guided through the second aperture 12. This prevents the object 2 from bending back on itself or becoming obstructed when it passes through the second aperture 12.

Figure 8:
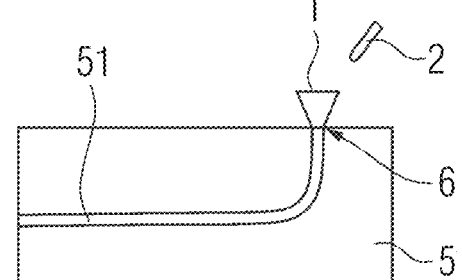

FIG. 8 shows an example embodiment of a guide apparatus 5 that includes a threading support facility 1 according to the invention.

The guide apparatus 5 includes an object guide 51. The object 2 is guided along this object guide 51 in the guide facility 5. The threading of the object 2 into the object guide 51 is simplified with the aid of the threading support facility 1. For this purpose, the threading support facility is connected to the guide apparatus 5 such that the second aperture 12 culminates in the object guide 51. The area of the second aperture 12 is exactly the same size as a cross-sectional area of the object guide 51 at the connection 6. In addition, the shapes of the two areas are identical. A transition without edges can therefore be provided for the object 2 from the threading support facility 1 into the object guide 51. The connection 6 can be embodied as a plug connection or a screw connection or a clamp connection or a clip connection or a rivet connection or a soldered connection or in one piece and so on.

In alternative embodiments, an intermediate fixture, which as described in the aforementioned, can be connected to the threading support facility and the guide apparatus, can be arranged between the threading support facility 1 and the guide apparatus 5. In particular, the intermediate fixture can include an object guide, which is a continuation of the object guide 51 of the guide apparatus and ends directly with the second aperture 12. In particular, the intermediate fixture can be connected to the second aperture 12 such that the connection is embodied to be without edges.

Where not yet explicitly implemented, yet appropriate and in the sense of the invention, individual example embodiments, individual sub-aspects or features thereof can be combined with one another or interchanged, without going beyond the scope of the present invention. Advantages of the invention described with regard to an example embodiment also apply, where transferable, to other example embodiments without their being mentioned specifically.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A threading support facility for threading an object into a guide apparatus, the threading support facility being connectable to the guide apparatus and being configured to support threading of the object into the guide apparatus, the threading support facility comprising:
   a wall connecting a first aperture of the threading support facility and a second aperture of the threading support facility,
      the first aperture being embodied as an inlet for insertion of the object into the threading support facility and the second aperture being embodied as an outlet out of the threading support facility, and
      a sub-guide running along the wall of the threading support facility and running in a direction from the first aperture to the second aperture, the sub-guide being configured to support guiding of the object, after insertion through the first aperture, into the threading support facility in a direction of the second aperture; and
   a plurality of sensors disposed along the sub-guide from the first aperture to the second aperture, each of the plurality of sensors including a transmitter on a first side of the sub-guide and a receiver on an opposite side of the sub-guide and each of the plurality of sensors being configured to monitor a sub-section of the sub-guide,
   wherein the sub-guide runs at least partly in a spiral shape around a connecting line between the first aperture and the second aperture.

2. The threading support facility of claim 1, wherein the sub-guide is embodied as at least one groove in the wall of the threading support facility.

3. The threading support facility of claim 2, wherein the first aperture is larger in area than the second aperture.

4. The threading support facility of claim 3, wherein the first aperture and the second aperture are connected by the wall, the wall being funnel shaped.

5. The threading support facility of claim 2, wherein at least one sensor of the plurality of sensors is configured to detect threading of the object through the threading support facility.

6. A guide apparatus comprising:
   the threading support facility of claim 2, the guide apparatus being embodied to guide the object.

7. The threading support facility of claim 1, wherein the first aperture is larger in area than the second aperture.

8. The threading support facility of claim 7, wherein the first aperture and the second aperture are connected by the wall, the wall being funnel shaped.

9. The threading support facility of claim 8, wherein at least one sensor of the plurality of sensors is configured to detect threading of the object through the threading support facility.

10. A guide apparatus comprising:
   the threading support facility of claim 8, the guide apparatus being embodied to guide the object.

11. The threading support facility of claim 1, wherein the sub-guide includes a first sub-aperture with a first area and a second sub-aperture with a second area, the second area being smaller than the first area, the first sub-aperture and the second sub-aperture being connected by a sub-wall with a tapered cross-sectional area, and the first sub-aperture being arranged on the first aperture of the threading support facility and the second sub-aperture being arranged on the second aperture of the threading support facility.

12. The threading support facility of claim 1, wherein at least one sensor of the plurality of sensors is configured to detect threading of the object through the threading support facility.

13. The threading support facility of claim 12, wherein the at least one sensor of the plurality of sensors includes at least one light sensor.

14. The threading support facility of claim 12, wherein the at least one sensor of the plurality of sensors includes an impedance sensor.

15. The threading support facility of claim 12, wherein the at least one sensor of the plurality of sensors includes an X-ray sensor.

16. The threading support facility of claim 1, further comprising:

a lubricant dispenser to dispense a lubricant to increase a sliding capacity of the object on the wall of the threading support facility.

17. The threading support facility of claim 1, wherein the object includes a magnetically active sub-region, the threading support facility further comprising:

at least one magnetically active sub-region arranged on the wall of the threading support facility.

18. The threading support facility of claim 17, wherein the at least one magnetically active sub-region is a multiplicity of magnetically active sub-regions, the multiplicity of magnetically active sub-regions being arranged along the sub-guide, the multiplicity of magnetically active sub-regions of the threading support facility being activatable independently and activatable to guide the magnetically active sub-region of the object in the threading support facility.

19. A guide apparatus comprising:

the threading support facility of claim 1, the guide apparatus being embodied to guide the object.

* * * * *